United States Patent
Wei et al.

(10) Patent No.: US 9,325,913 B2
(45) Date of Patent: Apr. 26, 2016

(54) RADIATION DETECTOR FOR USE IN SEQUENTIAL IMAGE ACQUISITION

(75) Inventors: Ching-Yeu Wei, Schenectady, NY (US); Jeffrey Wayne Eberhard, Albany, NY (US); George Edward Possin, Schenectady, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 958 days.

(21) Appl. No.: 13/339,222

(22) Filed: Dec. 28, 2011

(65) Prior Publication Data

US 2013/0170615 A1   Jul. 4, 2013

(51) Int. Cl.
| | |
|---|---|
| *G01N 23/04* | (2006.01) |
| *G01T 1/00* | (2006.01) |
| *G01T 1/20* | (2006.01) |
| *G01T 1/24* | (2006.01) |
| *A61B 6/00* | (2006.01) |
| *H04N 5/32* | (2006.01) |
| *H01L 31/00* | (2006.01) |
| *G01J 1/00* | (2006.01) |
| *H04N 5/361* | (2011.01) |

(52) U.S. Cl.
CPC .. *H04N 5/32* (2013.01); *A61B 6/42* (2013.01); *A61B 6/4233* (2013.01); *G01J 1/00* (2013.01); *G01N 23/04* (2013.01); *G01T 1/2018* (2013.01); *G01T 1/24* (2013.01); *H01L 31/00* (2013.01); *H04N 5/361* (2013.01); *A61B 6/4208* (2013.01); *A61B 6/482* (2013.01)

(58) Field of Classification Search
CPC . G01T 1/16–1/28; G01T 1/2018; G01T 1/24; H04N 5/32; A61B 6/42; A61B 6/4233; A61B 6/482; A61B 6/4208; G01N 23/04; H01L 31/00; G01J 1/00
USPC .................................................. 378/98.8, 62
See application file for complete search history.

(56) References Cited

U.S. PATENT DOCUMENTS

| | | | |
|---|---|---|---|
| 5,432,334 | A | 7/1995 | Nelson et al. |
| 7,203,274 | B2 | 4/2007 | Charles, Jr. et al. |
| 7,688,936 | B2 | 3/2010 | Toth |
| 7,953,207 | B2 | 5/2011 | Ohta et al. |
| 2004/0156473 | A1* | 8/2004 | Nonaka et al. ............ 378/62 |
| 2006/0067471 | A1* | 3/2006 | Hopkins et al. ........ 378/98.8 |
| 2007/0104311 | A1* | 5/2007 | Possin et al. ............ 378/19 |
| 2007/0153109 | A1* | 7/2007 | Lule ....................... 348/308 |

(Continued)

FOREIGN PATENT DOCUMENTS

| | | |
|---|---|---|
| EP | 817546 A1 | 7/1998 |
| EP | 2258269 A1 | 8/2010 |
| WO | 0068710 A2 | 11/2000 |
| WO | 2009102839 A2 | 8/2009 |

(Continued)

OTHER PUBLICATIONS

Ruetten et al. (WO 2009/156927), High Dynamic Range X-ray Detector with Improved Signal to Noise Ratio. Dec. 30, 2009.*

*Primary Examiner* — David J Makiya
*Assistant Examiner* — Dani Fox
(74) *Attorney, Agent, or Firm* — Fletcher Yoder, P.C.

(57) ABSTRACT

A radiation detector is provided that provides fast sequential image acquisition. In one embodiment, the radiation detector a diode capacitor that is charged in response to a radiation exposure event. The charge stored in the diode capacitor is transferred to a separate storage capacitor, allowing a new charge to be generated and stored at the diode capacitor.

19 Claims, 5 Drawing Sheets

(56) References Cited

U.S. PATENT DOCUMENTS

2008/0149843 A1* 6/2008 Tredwell ................. 250/370.11
2010/0098217 A1 4/2010 Caiafa et al.

FOREIGN PATENT DOCUMENTS

WO WO2009/156927 * 12/2009
WO 2010111697 A2 9/2010

* cited by examiner

RADIATION DETECTOR FOR USE IN SEQUENTIAL IMAGE ACQUISITION

BACKGROUND

Non-invasive imaging technologies allow images of the internal structures of a subject (e.g., a patient or object) to be obtained without performing an invasive procedure on the patient or object. Non-invasive imaging systems may operate based on the transmission and detection of radiation through or from a subject of interest (e.g., a patient or article of manufacture). For example, X-ray based imaging techniques (such as mammography, fluoroscopy, computed tomography (CT), and so forth) typically utilize an external source of X-ray radiation that transmits X-rays through a subject and onto a detector disposed opposite the X-ray source that detects the X-rays transmitted through the subject.

In such radiation-based imaging approaches, the radiation detector is an integral part of the imaging process and allows the acquisition of the radiation transmission data used to generate the images or data of interest. In certain radiation detection schemes, the radiation may be detected by use of a scintillating material that converts the higher energy radiation (e.g., X-rays) to optical light photons (e.g., visible light), which can then be detected by photodetector devices, such as photodiodes.

In certain implementations, it may be useful to obtain radiation transmission information for different wavelengths or spectra of the radiation. In particular, the differential transmission of radiation at different energies may provide useful information about the composition of the materials through which the radiation is passing. In such implementations, two or more energy levels or spectra of radiation may be used to obtain this differential transmission information, with separate images acquired at each energy. In conventional approaches, multi-energy images are normally taken by repeating the same procedure, which is exposure and subsequent readout for each X-ray energy, due to: (1) slow switching speed between each energy and (2) the image sensor employed can store only one image at a time. However, existing detection schemes may prove limiting in such multi-energy applications. For example, in instances where the imaging context is rapidly changing or otherwise dynamic (e.g., in cardiac applications, in interventional implementations, or where a dissipating contrast agent is employed), the speed at which sequential images at different energies are acquired may be insufficient due to the speed at which the detector may be read out and readied for subsequent image acquisition.

BRIEF DESCRIPTION

In accordance with one embodiment, a radiation detector is provided. The radiation detector comprises a plurality of pixels. Each pixel includes a photodiode with an associated diode capacitor. The diode capacitor is charged when the photodiode is exposed to light. Each pixel also includes a storage capacitor and a transfer gate configured to control a flow of charge between the diode capacitor and the storage capacitor. Each pixel also includes a matrix switch transistor configured to control readout of the storage capacitor.

In accordance with another embodiment, an imaging system is provided. The imaging system comprises an X-ray source configured to emit X-rays and a detector configured to generate signals in response to X-rays incident on the detector. The detector comprises a plurality of detector elements. Each detector element comprises a photodiode and a first capacitor that is charged when the photodiode is exposed to light. Each detector element also comprises a second capacitor and a transfer gate configured to control a flow of charge between the first capacitor and the second capacitor. Each detector element also comprises a matrix switch transistor configured to control readout of the second capacitor. The imaging system also comprises a data acquisition system configured to selectively read out detector elements of the detector, wherein reading out detector elements comprises at least determining a charge stored in the second capacitor.

In accordance with a further embodiment, a method for acquiring non-invasive image data is provided. The method includes the act of generating a first charge at a diode capacitor of a detector element of a radiation detector. The first charge is transferred from the diode capacitor to a storage capacitor. A second charge is generated at the diode capacitor. The first charge is read out from the storage capacitor. The second charge is transferred from the diode capacitor to the storage capacitor. The second charge is read out from the storage capacitor.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Figure 1:
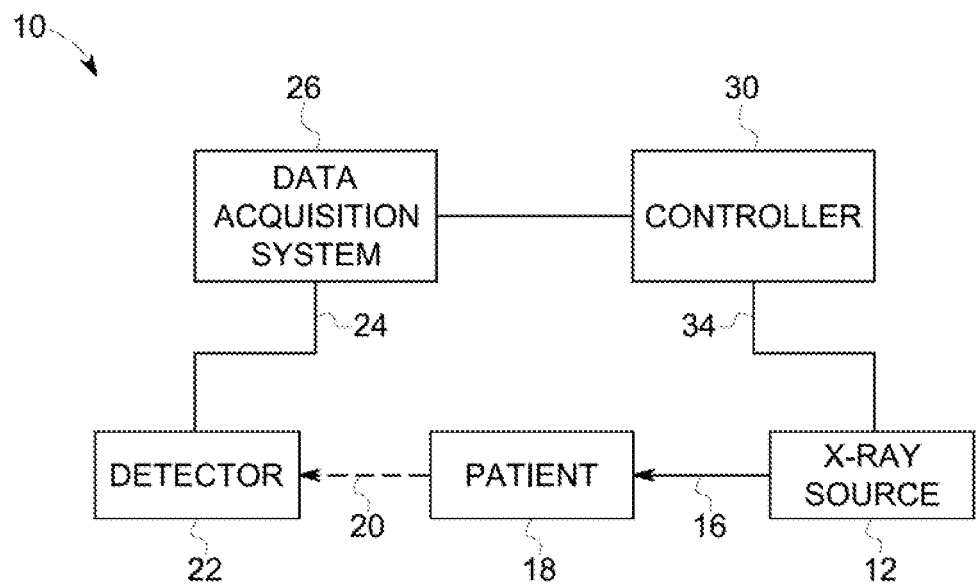
FIG. 1 is a block diagram illustrating an embodiment of an X-ray imaging system comprising a detector in accordance with an aspect of the present disclosure.

The present disclosure addresses certain of the issues noted above. In particular, with respect to multi-energy imaging, such as dual-energy techniques, different applications may present different issues. For example, the goals and issues related to standard radiographic dual-energy imaging (e.g., reduction of high attenuation structures, such as bones, to better view soft tissue), to computed tomography (CT) dual-energy imaging (e.g., quantifying information about material differences in clinical structures of interest), and to interventional dual-energy imaging (e.g., segmentation of interventional tools and contrast agents from surrounding tissues) may impose different constraints and requirements on a dual energy system or the components of such a system, such as the radiation detecting component.

By way of example, in an interventional imaging application, motion of the anatomy during imaging, such as respiratory or bowel gas related motion of the abdomen, cardiac motion in the thoracic cavity, or the motion of interventional tools during the procedure, may present challenges to identifying, segmenting, or otherwise tracking an interventional tool (e.g., a stent of catheter guidewire) during imaging. In the presence of motion, conventional (i.e., single-energy) imaging procedures of acquiring a prior "mask" image of the anatomy before an interventional event (such as contrast agent injection), and using the mask image in conjunction with a post-event image to perform subtracted imaging is ineffective. That is, because the anatomy is moving during the procedure, the "mask" image no longer corresponds to the background anatomy after a short interval of time has expired.

In this interventional context, certain of these issues may be addressed by using dual or multi-energy approaches that allow differentiation of different material compositions so that interventional materials (such as an injected contrast agent) can be discriminated from anatomical structure. For example, dual energy decomposition of two sequential, adjacent images (e.g., a high energy (i.e., high kVp) image and a low energy (i.e., low kVp) image) in a fluoroscopy sequence may allow interventional and anatomical structures to be differentiated. In one example, of such a fluoroscopy sequence, separates images (i.e., frames) may be acquired at a rate of approximately 30 frames per second (fps). Such an approach may allow the time between the two processed images to be reduced from as much as several seconds to on the order of tens of milliseconds, and may significantly reduce any motion issues in the imaging.

However, even in such a dual-energy fluoroscopy approach, the time between sequential high and low kVp images acquired at 30 fps, leaves a latency of approximately 33 msec between frames. Such a latency may be unsuitable in contexts where fast moving anatomy is being imaged, such as in a cardiac imaging application. For example, for structures moving at 1 cm/sec, the net motion between frames acquired at 30 fps can be as much as 0.3 mm, or about 1.5 pixels for a standard flat panel detector used in these applications. This offset may be unsuitable in a dual-energy decomposition application and/or where it is desired to freeze the anatomical motion. As discussed herein, a detector technology that enables a reduction in the time between acquisition of pairs of high kVp and low kVp images is disclosed. In particular, in accordance with various disclosed embodiments, a sequence or series of radiation exposure events may be performed without an intervening readout of the detector electronics between the exposure events (i.e., a second exposure event may occur prior to reading out the stored charge associated with a first exposure event). In this manner, in one implementation a latency between radiation exposure events of 1 msec or less may be achieved. Further, it should be appreciated that the detector technology described herein may be extended to the generation of more than a pair of images (i.e., three or more separate images in a sequence or set) and may be used in contexts other than dual- or multi-energy imaging.

It should also be noted that the present approaches may be utilized in a variety of imaging contexts, such as in medical imaging, product inspection for quality control, and for security inspection, to name a few. However, for simplicity, examples discussed herein relate generally to medical imaging, particularly X-ray based imaging techniques, such as: computed tomography (CT), mammography, tomosynthesis, C-arm angiography, conventional X-ray radiography, and fluoroscopy. However, it should be appreciated that these examples are merely illustrative and are discussed merely to simplify explanation and to provide context for examples discussed herein. That is, the present approaches may be used in conjunction with any suitable radiation-based approaches and in contexts other than medical imaging.

With the foregoing in mind, FIG. 1 provides a block diagram illustration of a generalized X-ray based imaging system 10. Specifically, FIG. 1 depicts an embodiment of a medical imaging system that may utilize an X-ray detector and acquisition circuitry, as discussed herein. The X-ray imaging system 10 may be an inspection system, such as for quality control, package screening, and safety screening, or may be a medical imaging system. The imaging system 10 includes a radiation detector 22 for detecting incident radiation, such as X-rays. The X-rays 16 may be emitted from a source 12 and directed toward a patient 18 or other subject undergoing non-invasive examination such that the transmitted X-rays 20 that pass through the patient 18 are incident on the detector 22.

In certain implementations, the source 12 may include one or more X-ray tubes or solid state emitting structures. In certain embodiments, the source 12 may be configured to emit X-rays 16 at two or more characteristic energy profiles or spectra (e.g., at a high kVp and a low kVp). In one implementation, the source 12 emits X-rays 16 at alternating high and low energy profiles such that alternating high and low energy images are acquired at the detector 22. That is, in one implementation, paired high and low energy images are generated by the system 10. In other implementations, the source 12 may generate and emit X-rays at more than two characteristic energy profile (such as at a high, a low, and a medium kVp). In addition, in certain implementations, the source 12 may not emit X-rays during the acquisition of one of a set of images at the detector 22 such that a "dark" or "dark current" image is generated as a baseline for assessing the noise intrinsic to the detector or ambient radiation present in the environment. In such an embodiment, the dark image may be used as an offset to provide image correction, even in single-energy implementations.

The detector 22 generates electrical signals 24 in response to the incident radiation 20, and these electrical signals 24 are sent through respective channels to a data acquisition system (DAS) 26. Once the DAS 26 acquires the electrical signals 18, which may be analog signals, the DAS 26 may digitize or otherwise condition the data for subsequent processing. For example, the DAS 26 may filter the image data based on time (e.g., in a time series imaging routine), may filter the image data for noise or other image aberrations, may perform a weighted subtraction between paired high and low energy images, may generate material or composition specific images, and so on. As will be appreciated, some or all of these functionalities may instead be performed by one or more processing components in communication with the DAS 26, such as the controller 30 discussed below or one or more workstations in communication with the DAS 26 and/or controller 30.

In one embodiment, the DAS 26 communicates with the controller 30, to which it is operatively connected. The controller 30 may be an application-specific or general purpose computer with appropriately configured software for performing and controlling operations of the imaging system 10. The controller 30 may include one or more of processing components (e.g., processors), memory circuitry, non-volatile storage components, and/or other computer circuitry configured to execute algorithms such as imaging protocols, data processing algorithms, diagnostic evaluation algorithms, and so forth. As an example, the controller 20 may direct the DAS 26 to perform image acquisition at certain times, to filter certain types of data, and the like. Additionally, the controller 30 may include features for interfacing, directly or indirectly, with an operator, such as an Ethernet connection, an Internet connection, a wireless transceiver, a keyboard, a mouse, a trackball, a display, and so on.

In system 10, to enable the collection of image data, the controller 30 is also operatively connected to the source 12 of X-rays 16. The controller 30 may furnish a variety of control signals, such as timing signals, imaging sequences, and so forth to the X-ray source 12 via a control link 34. In some embodiments, the control link 34 may also furnish power, such as electrical power, to the X-ray source 12 via control link 34.

In conventional approaches, the system of FIG. 1 may be used in a single-energy or in a multi- or dual-energy context. In a conventional dual-energy application using such a system, a pair of dual energy images may consist of a high-energy X-ray exposure after which the detector 22 is read out to generate a high-energy image. Generation and readout of the high-energy image may then be followed by a low-energy X-ray exposure event and the subsequent readout of the detector 22 to generate a low-energy image. As discussed herein, such an approach may be characterized as a "shoot-read-shoot-read" approach in which the detector 22 is read out between each separate X-ray exposure event. Such a conventional approach may not be suitable for imaging fast moving objects (such as a beating heart) due to the time delay (approximately 35 msec) between exposure events attributable to the intervening readout of the detector 22 to generate the first image.

Figure 2:
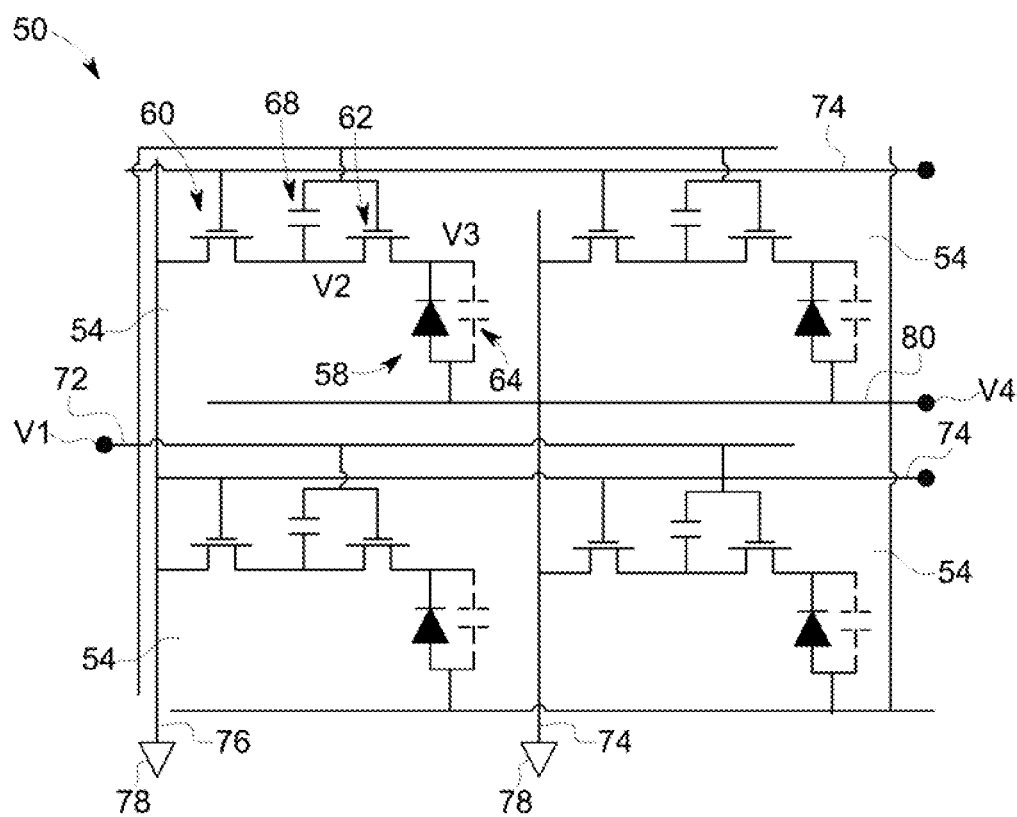
FIG. 2 is a circuit view of detector elements of a detector in accordance with an aspect of the present disclosure.

In accordance with the present approach, an alternative X-ray detector 22 architecture and acquisition sequence is employed. Turning to FIG. 2, an embodiment of a circuit view of a detector architecture in accordance with the present approach is depicted. In this circuit, two images, such as a high-energy image and a low-energy image (or an illuminated image and a dark image), may be sequentially generated and the corresponding charges stored on the detector panel. Both images may then subsequently be read out. Thus, instead of a "shoot-read-shoot-read" acquisition sequence, the image acquisition sequence instead generally corresponds to a "shoot-shoot-read-read" sequence. As a result, the time between the separate exposure events associated with the two images (i.e., the "shoot" steps) is reduced from approximately 35 milliseconds (msec) to a range of microseconds (μsec), such as 1 μsec to 100 μsec, due to not performing an intervening readout of the detector assembly 22 between exposures. In particular, the time delay between the separate exposure events, when using the detector architecture disclosed herein, corresponds to the speed at which the source 12 can switch between the two or more different energy profiles being employed in the imaging application (typically on the order of microsecond for an X-ray tube) rather than the speed with which the detector 22 can be readout and readied for a subsequent image or frame capture. Delays on the order of microseconds will substantially eliminate motion blur, and thereby improve image quality in dynamic imaging contexts involving fast motion and/or contrast dispersal (such as cardiac imaging applications).

With this in mind and turning to FIG. 2, one possible embodiment of a detector circuit 50 in accordance with the present disclosure is depicted. It may be initially noted that the embodiment depicted by circuit 50 of FIG. 2 differs from a conventional detector panel (depicted in FIG. 3), which has one field-effect transistor (FET) (matrix switch transistor 60) and one capacitor (diode capacitor $C_1$ 64) per detector pixel 54. Instead, a present embodiment of a detector architecture, as depicted in FIG. 2, an additional FET (transfer gate 62) and an additional capacitor (C2) 68 are inserted between the matrix switching transistor 60 and the photosensitive diode 58 of each pixel 54, as discussed below.

Figure 3:
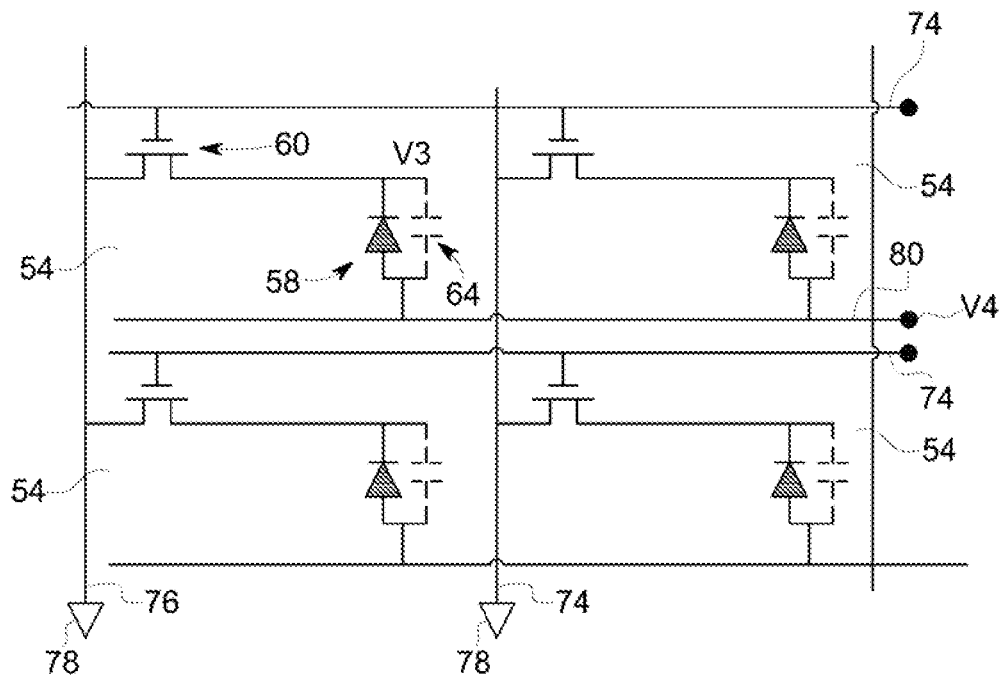
FIG. 3 is a circuit view of prior art detector elements of a detector.
Figure 4:
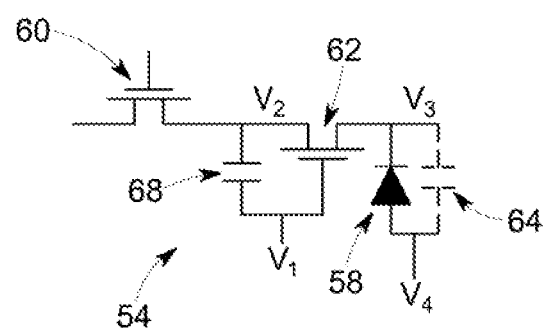
FIG. 4 is a circuit view of a single detector element in accordance with an aspect of the present disclosure.
Figure 5:
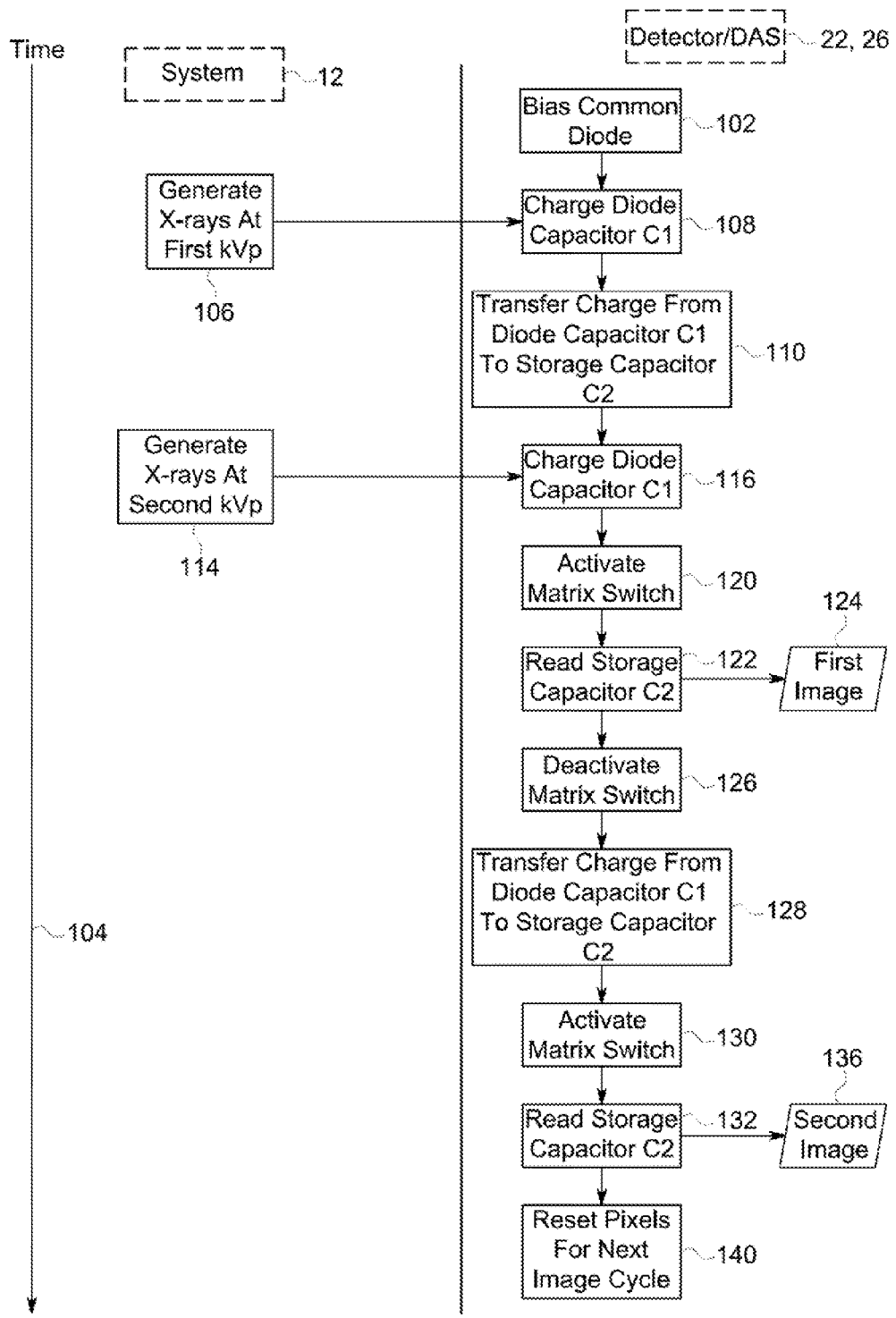
FIG. 5 depicts a flow diagram of actions performed at or on a source and detector, in accordance with an aspect of the present disclosure.

In addition, the depicted implementation of circuit 50 includes one extra lead 72, for applying a transfer gate voltage, $V_1$, in addition to the matrixed scan lines 74 and matrixed data lines 76 (shown with amplifier 78) that are used in combination to selectively apply voltages $V_2$ and $V_3$, and in addition to the common diode line 80 used to apply common diode bias $V_4$ in a conventional X-ray detector panel (FIG. 3). That is, in a conventional implementation, scan lines 74 and data lines 76 are present and are matrixed to selectively activate individual pixels 54 by application of voltages $V_2$ and $V_3$ while a common diode bias $V_4$ is applied to all pixels 54. In the circuit 50 of the depicted embodiment of FIG. 2, an additional common voltage in the form of transfer gate voltage $V_1$ is also applied across all pixels 54. Turning to FIG. 4, a close up of a pixel 54 is depicted in accordance with the embodiment of FIG. 2, With the foregoing examples in mind and with reference to FIGS. 2 and 4, FIG. 5 depicts a flow diagram of steps performed at the source 12, detector 22, and/or data acquisition system 26 in one implementation of an image acquisition sequence 100 using a detector architecture as discussed herein. In this depicted example, the common diode bias $V_4$ at the detector 22 is initially fixed (block 102) at a negative voltage (e.g., −8 V to −10 V) in preparation for image acquisition. Subsequently, as evidenced by time-line 104, when the detector 22 is determined to be ready for image capture the source 12 emits (block 106) X-rays 16 at a first energy profile (in a dual-energy acquisition), resulting in charge accumulating (block 108) at the respective diode capacitor $C_1$ 64 associated with each photodiode 58. The charge accumulated at each pixel 54 corresponds to the incidence of the X-rays at the first energy profile at the respective pixel 54.

The voltage $V_1$ is pulled from a large negative off voltage (e.g., about −8 V) to a threshold voltage $V_T$ associated with the n-channel MOSFET (NMOS). In this example, the $V_T$ can be assumed to be 0 V and $V_T$ can be added to all bias voltages to account for non-zero values of $V_T$. This change in bias $V_1$ results in the charge being transferred (block 110) from diode capacitor $C_1$ 64 to a storage capacitor $C_2$ 68. In one implementation, the transfer efficiency exceeds 99%. The transfer of charge is complete, in one embodiment, when the transistor shuts off at $V_1 - V_3 = V_T$.

Subsequent to charge transfer from $C_1$ 64 to $C_2$ 68, the X-ray source 12 emits (block 114) X-rays 16 at a second energy profile (in a dual-energy acquisition), resulting in a new charge accumulating (block 116) at the respective diode capacitor $C_1$ 64 associated with each photodiode 58. The new charge accumulated at each pixel 54 corresponds to the incidence of the X-rays at the second energy profile at the pixel 54. Thus, after the second exposure event, charge is stored at both diode capacitor $C_1$ 64 (corresponding to the most recent exposure event) and storage capacitor $C_2$ 68 corresponding to the initial exposure event).

In the depicted example, the matrix switch transistors 60 are activated (block 120) selectively to allow readout (block 122) of the storage capacitor $C_2$ 68 of each pixel 54. The readout signals of each pixel 54 together correspond to, or are used to derive, the first image 124, such as a high- or low-energy image. After readout of the storage capacitors $C_2$ 68, the matrix switch transistors 60 are then deactivated (block 126) and the charge present in diode capacitor $C_1$ 64 is transferred (block 128) to storage capacitor $C_2$ 68, as discussed above.

Figure 6:
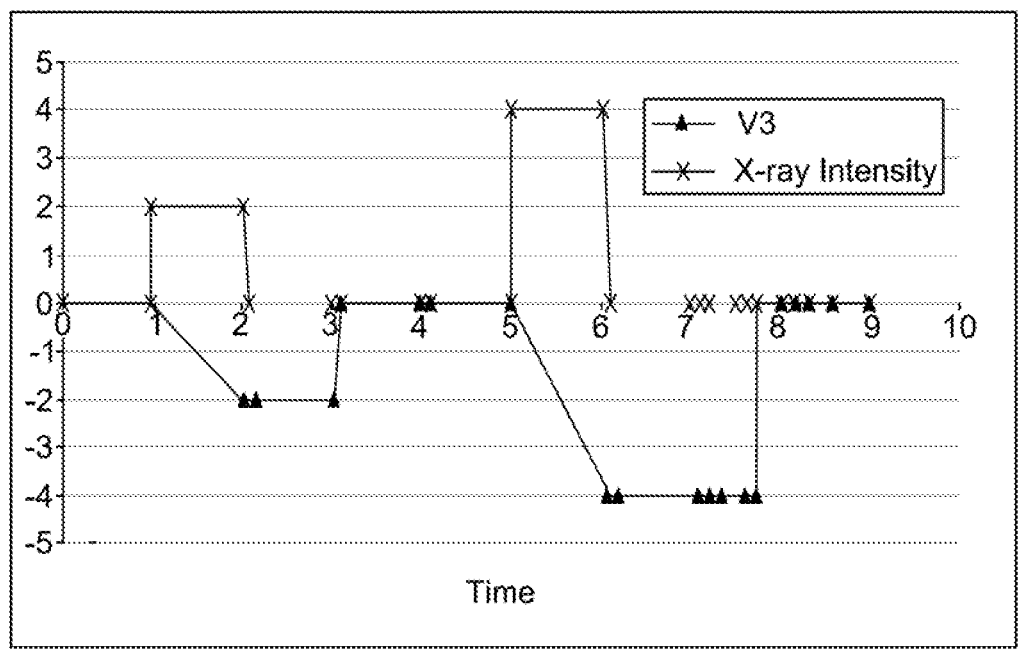
FIG. 6 is a time-bias plot, in accordance with an aspect of the present disclosure.
Figure 7:
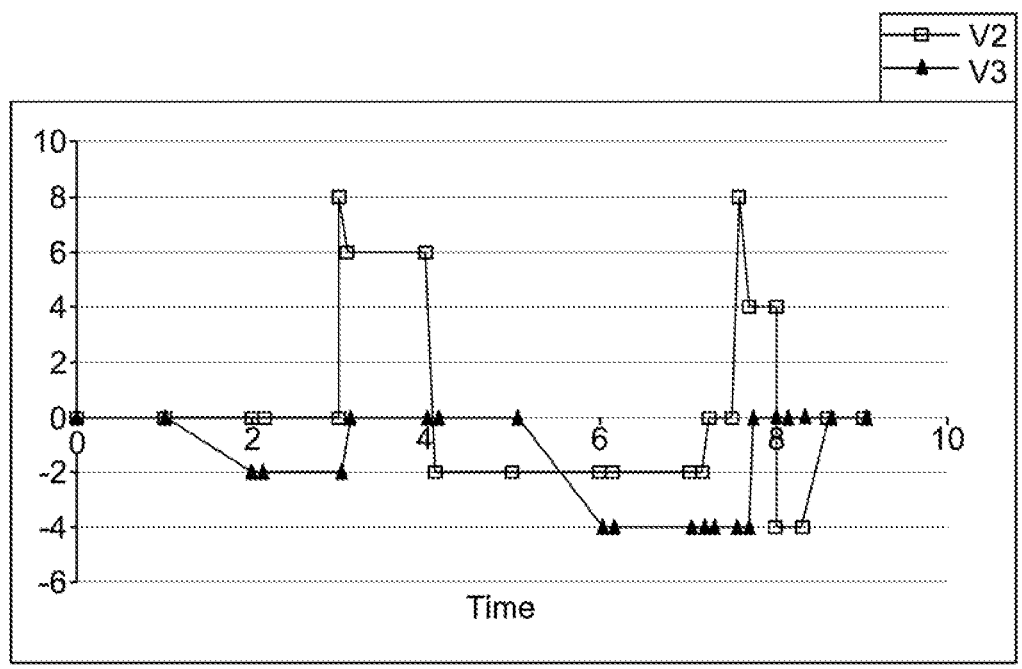
FIG. 7 is a time-bias plot, in accordance with a further aspects of the present disclosure.
Figure 8:
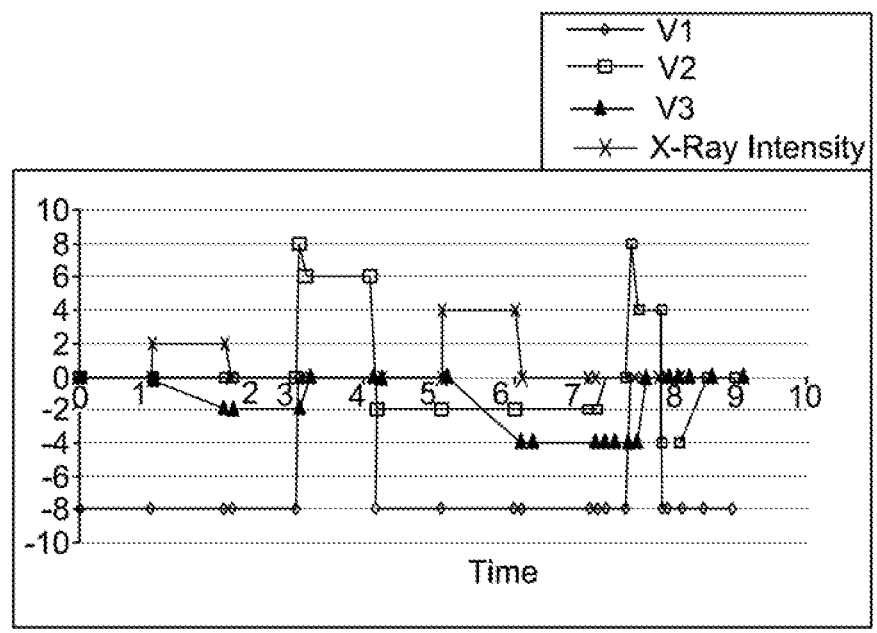
FIG. 8 is a time-bias plot, in accordance with a additional aspects of the present disclosure.

The matrix switch transistors 60 are reactivated (block 130) selectively to allow readout (block 132) of the storage capacitor $C_2$ 68 of each pixel 54. The readout signals of each pixel 54 together correspond to, or are used to derive, the second image 136, such as a high- or low-energy image, and so forth. The pixels 54 may subsequently be reset (block 140) for another image acquisition cycle With the foregoing in mind, the following Table 1, in conjunction with FIGS. 6-8, provides an example of a suitable operating time-bias sequence for X-ray exposure and suitable voltage levels for the detector architecture discussed herein.

TABLE 1

| Light Intensity | Time (sec) | $V_1$ (V) | $V_2$ (V) | $V_3$ (V) | $V_4$ (V) | Matrix Switch | Comments |
|---|---|---|---|---|---|---|---|
| 0 | 0 | −8 | 0 | 0 | −10 | off | |
| 0 | 1 | −8 | 0 | 0 | −10 | off | |
| 2 | 1.01 | −8 | 0 | 0 | −10 | off | First exposure starts |
| 2 | 2 | −8 | 0 | −2 | −10 | off | First exposure stops |
| 0 | 2.1 | −8 | 0 | −2 | −10 | off | Hold |
| 0 | 3 | −8 | 0 | −2 | −10 | off | Hold |
| 0 | 3.01 | 0 | 8 | −2 | −10 | off | Start Transfer to $C_2$ |
| 0 | 3.1 | 0 | 6 | 0 | −10 | off | Transfer complete: transistor shuts off at $V_1 - V_3 = V_T$ |
| 0 | 3.11 | 0 | 6 | 0 | −10 | off | Hold |
| 0 | 4 | 0 | 6 | 0 | −10 | off | Hold |
| 0 | 4.1 | −8 | −2 | 0 | −10 | off | Setup for second Exposure |
| 0 | 5 | −8 | −2 | 0 | −10 | off | Setup for second Exposure |
| 4 | 5.01 | −8 | −2 | 0 | −10 | off | Second exposure starts |
| 4 | 6 | −8 | −2 | −4 | −10 | off | Second exposure stops |
| 0 | 6.1 | −8 | −2 | −4 | −10 | off | Hold |
| 0 | 7 | −8 | −2 | −4 | −10 | off | Hold |
| 0 | 7.1 | −8 | −2 | −4 | −10 | on | Read charge on $C_2$ |
| 0 | 7.2 | −8 | 0 | −4 | −10 | on | Read charge on $C_2$ |
| 0 | 7.5 | −8 | 0 | −4 | −10 | off | Hold |
| 0 | 7.6 | 0 | 8 | −4 | −10 | off | Transfer charge from $C_1$ to $C_2$ |
| 0 | 7.7 | 0 | 4 | 0 | −10 | off | Transfer complete: transistor shuts off at $V_1 - V_3 = V_T$ |
| 0 | 8 | 0 | 4 | 0 | −10 | off | Hold |
| 0 | 8.01 | −8 | −4 | 0 | −10 | off | Reset diode |
| 0 | 8.1 | −8 | −4 | 0 | −10 | off | Reset diode |
| 0 | 8.3 | −8 | −4 | 0 | −10 | on | Read charge on $C_2$ |
| 0 | 8.6 | −8 | 0 | 0 | −10 | on | Read charge on $C_2$ |
| 0 | 9 | −8 | 0 | 0 | −10 | | Reset for next cycle |

While the foregoing has generally been described in the context of a dual-energy acquisition to simplify explanation, it should be appreciated that, as noted above, the present detector architecture may be employed in other contexts. For example, embodiments of the present detector architecture may be employed in applications where images or frames are acquired at a single energy or illumination, but a corresponding "dark" frame or frame is acquired in alternating sequence with each illuminated image or frame. In such an application, no second X-ray emission by the source 12 may occur, but instead intrinsic detector noise and/or ambient or environmental radiation is allowed to accumulate charge at the diode capacitor $C_1$ 64 for the length of time typically associated with an exposure event. This charge may then be read out as corresponding to the second (or first image). Dark images so acquired may be used in various noise and/or artifact reduction applications or as part of an ongoing or periodic calibration process.

Similarly, though a dual-energy example has been provided to simplify explanation, it should be appreciated that the present detector architecture can be modified so as to facilitate fast image acquisition using more than two energy profiles (such as a low-, medium-, and high-energy profile) or using two energy profiles plus acquiring a dark image with each pair of high and low energy images.

Figure 9:
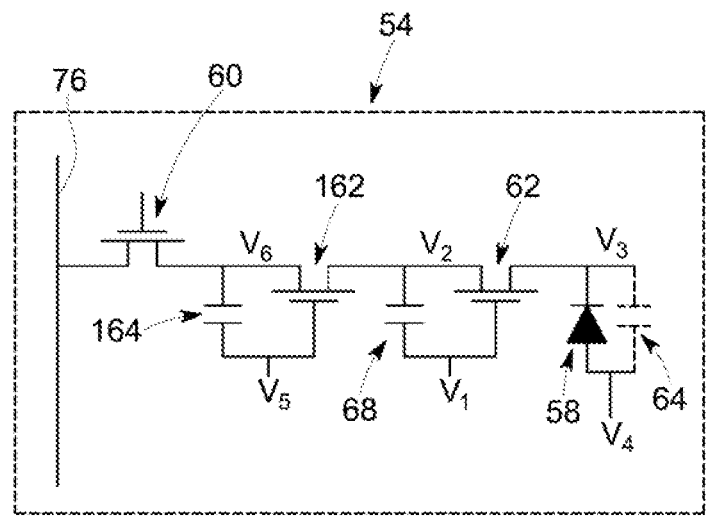
FIG. 9 is a circuit view of a single detector element in accordance with further aspects of the present disclosure.

For example, turning to FIG. 9, an example of an embodiment suitable for acquiring more than three sequential exposures without an intervening readout operation is depicted. In this embodiment, an additional storage capacitor $C_3$ 164 is provided in conjunction with an additional FET (i.e., transfer gate 162). In an example of a multi-image acquisition using the circuit depicted in FIG. 9, an X-ray exposure cycle may be started and an X-ray source 12 turned on to generate a first X-ray exposure (such as at a first energy) corresponding to a first image to be acquired. A charge corresponding to this first exposure is integrated in diode capacitor 64 and the X-ray source 12 is switched off. Transistor 62 is turned on by biasing $V_1$ and the charge associated with the first exposure event is transferred from the diode capacitor 64 to storage capacitor 68. Transistor 62 is turned off by biasing $V_1$. Subsequently, transistor 162 (i.e., additional transfer gate 162) is turned on by biasing $V_5$ and the charge stored in storage capacitor 68 (corresponding to the first exposure event) is transferred to additional storage capacitor 164. After this charge is transferred, transistor 162 is switched off by biasing $V_5$.

With respect to the second exposure event, the X-ray source 12 is turned on, such as at a different energy level or profile, and charge corresponding to this second exposure event, is integrated in diode capacitor 64. When the source 12 is switched off, transistor 62 is switched on by biasing $V_1$. The charge corresponding to the second exposure event is transferred from the diode capacitor 64 to the storage capacitor 68 and the transistor 62 is switched off by biasing $V_1$. Thus, after this transfer event, the charge associated with the first exposure event is stored in additional storage capacitor 164 and the charge associated with the second exposure event is stored in storage capacitor 68.

With respect to the third exposure event, the X-ray source 12 is turned on again, such as at a different energy level or profile, and charge corresponding to this third exposure event, is integrated in diode capacitor 64. When the X-ray source is turned off, the X-ray exposure cycle is ended and the readout cycle is begun. At this point, the charge associated with the first exposure event is stored in additional storage capacitor 164, the charge associated with the second exposure event is stored in storage capacitor 68, and the charge associated with the third exposure event is stored in diode capacitor 64.

For readout, matrix switch transistor 60 at pixel 54 is turned on and the charge associated with the first exposure event, stored in additional storage capacitor 164, is read out to data line 76. Matrix switch transistor 60 at pixel 54 is turned off and this readout process is repeated for each pixel until the entire first image is read out.

To read out the second image, transistor 162 is turned on by biasing $V_5$ and the charge from storage capacitor 68 is transferred to additional storage capacitor 164. Transistor 162 is turned off by biasing $V_5$. Transistor 62 is turned on by biasing $V_1$ and the charge from diode capacitor 64 is transferred to storage capacitor 68. Transistor 62 is turned off by biasing $V_1$. Matrix switch transistor 60 is turned on and the charge associated with the second exposure event, now stored in additional storage capacitor 164, is read out to data line 76. Matrix switch transistor 60 at pixel 54 is turned off and this readout process is repeated for each pixel until the entire second image is read out.

To read out the third image, transistor 162 is turned on by biasing $V_5$ and the charge from storage capacitor 68 is transferred to additional storage capacitor 164. Transistor 162 is turned off by biasing $V_5$. Matrix switch transistor 60 is turned on and the charge associated with the third exposure event, now stored in additional storage capacitor 164, is read out to data line 76. Matrix switch transistor 60 at pixel 54 is turned off and this readout process is repeated for each pixel until the entire third image is read out. In this manner, a "shoot-shoot-shoot-read-read-read" operation may be performed with a latency measured in microsecond between the three exposure events. As discussed with respect to FIG. 9, three conductors ($V_1$, $V_4$, and $V_5$) are provided corresponding to three separate common electrodes to all of the array pixels in the imager panel. More generally, there will be n common electrodes for an n-energy imager panel as discussed herein. Further, as will be appreciated, the pixel 54 may be further modified to accommodate additional storage in this manner (such as to accommodate acquisition of four or more exposure events).

Technical effects of the invention include a detector architecture suitable for storing an additional charge such that sequential radiation exposures may be performed on a subject without an intervening readout of the detector panel. Sequential readout operations may subsequently be performed to retrieve the image data associated with each exposure event. One technical effect is the acquisition of sequential images or frame having a latency or delay between image exposure events that is less than 35 msec and, in some implementations, on the order of microseconds.

This written description uses examples to disclose the present approach, including the best mode, and also to enable any person skilled in the art to practice the disclosed subject matter, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A radiation detector, comprising:
    a plurality of detector elements, each detector element comprising:
        a photodiode with an associated diode capacitor, wherein the diode capacitor is charged when the photodiode is exposed to light;
        a storage capacitor;
        a transfer gate configured to control a flow of charge between the diode capacitor and the storage capacitor after exposure of the radiation detector to X-rays at a first energy spectrum, wherein a first lead applies a first voltage to the transfer gate during operation of the radiation detector; and
        a matrix switch transistor configured to control readout of the storage capacitor after exposure of the detector to X-rays at a second energy spectrum different from the first energy spectrum, wherein a respective scan line and a respective data line in combination apply respective second and third voltages to selectively activate the respective matrix switch transistor to allow separate readouts of the storage capacitor corresponding to the first energy spectrum and the second energy spectrum respectively during operation of the radiation detector.

2. The radiation detector of claim 1, wherein the first voltage is a common transfer gate voltage.

3. The radiation detector of claim 1, wherein each detector element is connected to a second lead configured to apply a common diode bias to each photodiode.

4. The radiation detector of claim 1, wherein the respective scan line is one of a plurality of scan lines and the respective data line is one of a plurality of data lines that, in combination, define a pixel matrix containing the plurality of detector elements.

5. The radiation detector of claim 1, wherein each detector element further comprises:
    an additional storage capacitor;
    an additional transfer gate configured to control a flow of charge between the diode capacitor and the additional storage capacitor; and
    an additional matrix switch transistor configured to control readout of the additional storage capacitor.

6. The radiation detector of claim 1, wherein the transfer gate comprises a field effect transistor.

7. The radiation detector of claim 1, wherein each detector element further comprises:
    an additional storage capacitor; and
    an additional transfer gate configured to control a flow of charge between the diode capacitor and the additional storage capacitor, wherein the matrix switch transistor is configured to control readout of the additional storage capacitor.

8. An imaging system, comprising:
    an X-ray source configured to emit X-rays at a first energy profile and at a second energy profile, different from a first energy profile;
    a detector configured to generate signals in response to X-rays incident on the detector, the detector comprising a plurality of detector elements, each detector element comprising:
        a photodiode;
        a first capacitor that is charged when the photodiode is exposed to light;
        a second capacitor;
        a transfer gate configured to control a flow of charge between the first capacitor and the second capacitor after exposure of the detector to X-rays at the first energy profile, wherein a first lead applies a first voltage to the transfer gate during operation of the radiation detector; and
        a matrix switch transistor configured to control readout of the second capacitor after exposure of the detector to X-rays at the second energy profile, wherein a respective scan line and a respective data line in combination apply respective second and third voltages to selectively activate the respective matrix switch transistor to allow separate readouts of the storage capacitor corresponding to the first energy profile and the second energy profile respectively during operation of the radiation detector; and
    a data acquisition system configured to selectively read out detector elements of the detector, wherein reading out detector elements comprises at least determining a charge stored in the second capacitor.

9. The imaging system of claim 8, comprising a controller in communication with the X-ray source and the data acquisition system.

10. The imaging system of claim 8, wherein the first voltage is a common transfer gate voltage.

11. The imaging system of claim 8, wherein each detector element is connected to a second lead configured to apply a common diode bias to each photodiode.

12. The imaging system of claim 8, wherein the respective scan line is one of a plurality of scan lines and the respective data line is one of a plurality of data lines that, in combination, define a pixel matrix containing the plurality of detector elements.

13. The imaging system of claim 8, wherein each detector element further comprises:
    a third capacitor;
    an additional transfer gate configured to control a flow of charge between the first capacitor and the third capacitor; and
    an additional matrix switch transistor configured to control readout of the third capacitor.

14. The imaging system of claim 8, wherein each detector element further comprises:
    a third capacitor; and
    an additional transfer gate configured to control a flow of charge between the first capacitor and the third capacitor, wherein an additional matrix switch transistor configured to control readout of the third capacitor.

15. A method for acquiring non-invasive image data, comprising:
    generating a first charge at a diode capacitor of a detector element of a radiation detector, wherein the first charge is generated in response to a first radiation exposure event having a first energy profile;
    transferring the first charge from the diode capacitor to a storage capacitor by applying a first voltage to a transfer gate;
    generating a second charge at the diode capacitor prior to reading out the first charge from the storage capacitor, wherein the second charge is generated in response to a second radiation exposure event having a second energy profile different from the first energy profile;
    reading out the first charge from the storage capacitor corresponding to the first energy profile while the second charge is stored in the diode capacitor by applying respective second and third voltages via a respective scan line and a respective data line to a matrix switching transistor;
    transferring the second charge from the diode capacitor to the storage capacitor by applying the first voltage to the transfer gate; and
    reading out the second charge from the storage capacitor corresponding to the second energy profile by applying the respective second and third voltages via the respective scan line and the respective data line to the matrix switching transistor.

16. The method of claim 15, wherein the first charge is generated in response to X-rays emitted by an X-ray source and the second charge is generated when the X-ray source is not emitting X-rays.

17. The method of claim 15, wherein reading out the first charge and reading out the second charge are initiated by activating a matrix switch transistor associated with the detector element.

18. The method of claim 15, wherein the time elapsed between generating the first charge at the diode capacitor and generating the second charge at the diode capacitor is less than 35 milliseconds.

19. The method of claim 15, comprising generating a first image based at least in part on the first charge read out from the storage capacitor and generating a second image based at least in part on the second charge read out from the storage capacitor.

* * * * *